US006630597B1

(12) United States Patent
Lin et al.

(10) Patent No.: US 6,630,597 B1
(45) Date of Patent: Oct. 7, 2003

(54) PHOTOCHROMIC 6-ARYL SUBSTITUTED 3H-NAPHTHO(2,1-B)PYRANS

(75) Inventors: Jibing Lin, Murrysville, PA (US); Barry Van Gemert, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 08/990,889

(22) Filed: Dec. 15, 1997

(51) Int. Cl.⁷ .......................... C07D 311/92; G02B 5/23
(52) U.S. Cl. .......................... 549/389; 252/586; 524/99; 524/109; 524/110
(58) Field of Search .......................... 549/389; 252/586; 524/99, 109, 110

(56) References Cited

U.S. PATENT DOCUMENTS

| | | | |
|---|---|---|---|
| 3,361,706 A | 1/1968 | Meriwether et al. | 260/39 |
| 3,562,172 A | 2/1971 | Ono et al. | 252/300 |
| 3,567,605 A | 3/1971 | Becker | 204/158 |
| 3,578,602 A | 5/1971 | Ono et al. | 252/300 |
| 3,627,690 A | 12/1971 | Casella et al. | 252/300 |
| 4,215,010 A | 7/1980 | Hovey et al. | 252/300 |
| 4,342,668 A | 8/1982 | Hovey et al. | 252/586 |
| 4,360,653 A | 11/1982 | Stevens et al. | 526/301 |
| 4,816,584 A | 3/1989 | Kwak et al. | 544/71 |
| 4,818,096 A | 4/1989 | Heller et al. | 351/163 |
| 4,826,977 A | 5/1989 | Heller et al. | 544/70 |
| 4,880,667 A | 11/1989 | Welch | 427/160 |
| 4,931,219 A | 6/1990 | Kwiatkowski et al. | 252/586 |
| 4,931,220 A | 6/1990 | Haynes et al. | 252/586 |
| 4,994,208 A | 2/1991 | McBain et al. | 252/586 |
| 5,066,818 A * | 11/1991 | Gemert et al. | 549/389 |
| 5,200,116 A * | 4/1993 | Heller | 252/586 |
| 5,200,483 A | 4/1993 | Selvig | 526/301 |
| 5,238,981 A | 8/1993 | Knowles | 524/110 |
| 5,274,132 A * | 12/1993 | Van Gemert | 549/389 |
| 5,373,033 A | 12/1994 | Toh et al. | 822/96 |
| 5,384,077 A | 1/1995 | Knowles | 252/586 |
| 5,405,958 A | 4/1995 | Van Gemert | 544/71 |
| 5,429,774 A | 7/1995 | Kumar | 252/586 |
| 5,458,814 A | 10/1995 | Kumar et al. | 252/586 |
| 5,466,398 A | 11/1995 | Van Gemert et al. | 252/586 |
| 5,475,074 A | 12/1995 | Matsuoka et al. | 526/336 |
| 5,514,817 A | 5/1996 | Knowles | 549/384 |
| 5,520,853 A | 5/1996 | Rickwood et al. | 252/586 |
| 5,552,090 A | 9/1996 | Van Gemert et al. | 252/586 |
| 5,552,091 A | 9/1996 | Kumar | 252/586 |
| 5,565,147 A | 10/1996 | Knowles et al. | 252/586 |
| 5,573,712 A | 11/1996 | Kumar et al. | 252/586 |
| 5,578,252 A | 11/1996 | Van Gemert et al. | 252/586 |
| 5,623,005 A | 4/1997 | Rickwood et al. | 524/96 |
| 5,628,935 A * | 5/1997 | Hughes et al. | 252/589 |
| 5,645,767 A | 7/1997 | Van Gemert | 252/586 |
| 5,808,100 A * | 9/1998 | Momoda et al. | 549/60 |

FOREIGN PATENT DOCUMENTS

JP  8-209119  *  8/1996

OTHER PUBLICATIONS

Olah et al., *Friedel–Crafts and Related Reactions*, Interscience Publishers, vol. 3, Chapter XXXI ("Aromatic Ketone Synthesis"), pp. 1–8, 1964.

Ishihara et al., "Regioselective Friedel–Drafts Acylation of 1,2,3,4-Tetrahydroquinoline and Related Nitrogen Heterocycles. Effect on NH Protective Groups and Ring Size", J. Chem. Soc. Perkins Trans. 1, 1992, pp. 3401–3406.

Hauser et al., Organic Reactions, vol. 8, pp. 59–61, 126–128 (1954).

Hauser et al., "A New Method for the Synthesis of Certain Benz[a]acridines", J. Amer. Chem. Soc., pp. 3858–3860 (1955).

Koptyug et al., "Reactions of Phenols with Lewis Acids II. Aralkylation of Aromatic Compounds by the Tautomeric Forms of Naphthols", Zh. Org. Khim., vol. 7, pp. 2398–2403 (1971).

Zhandov, et al., "2–Benzopyrylium Salts 33. 4–1'–Dimerization of 2–Benzopyrylum Salts. Formation of Benz[a]anthracenes", Khim. Get. Soed., No. 9, pp. 1185–1189 (translation) (1988).

* cited by examiner

*Primary Examiner*—Laura L. Stockton
(74) *Attorney, Agent, or Firm*—Frank P. Mallak

(57) ABSTRACT

Described are novel photochromic 6-aryl substituted 3H-naphtho[2,1-b]pyran compounds, examples of which are naphthopyran compounds having a substituted aryl group at the number 6 carbon atom and certain substituents at the 3-position of the pyran ring. Certain substituents may also be present at the number 7, 8, 9 or 10 carbon atoms of the compounds. These compounds may be represented by the following graphic formula:

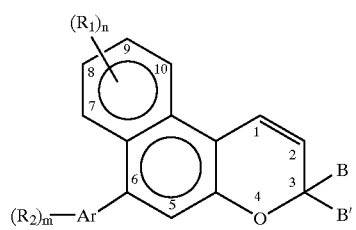

Also described are polymeric organic host materials that contain one or more of such compounds or combinations of such compounds) with complementary photochromic compounds, e.g., other naphthopyrans, benzopyrans and spiro(oxazine)type compounds.

22 Claims, No Drawings

PHOTOCHROMIC 6-ARYL SUBSTITUTED 3H-NAPHTHO(2,1-B)PYRANS

DESCRIPTION OF THE INVENTION

The present invention relates to certain novel naphthopyran compounds. More particularly, this invention relates to novel photochromic 6-aryl substituted 3H-naphtho[2,1-b] pyran compounds and to compositions and articles containing such novel naphthopyran compounds. When exposed to light radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion. U.S. Pat. No. 4,818,096 discloses purple/blue coloring photochromic benzo- or naphthopyrans having at the position alpha to the oxygen of the pyran ring a phenyl group having a nitrogen containing substituent in the ortho or para positions.

Certain photochromic naphtho[2,1-b]pyrans having a nitrogen-containing group at the 6 position of the naphthyl portion of the naphthopyran compound have been disclosed. U.S. Pat. No. 5,552,090 describes photochromic naphtho[2,1-b]pyrans substituted at the 6 position of the naphthyl portion of the naphthopyran compound with a nitrogen-containing heterocyclic ring. Photochromic naphtho[2,1-b] pyrans substituted at the 6 position of the naphthyl portion with an alkoxy group or aryloxy group are described in U.S. Pat. No. 5,520,853. U.S. Pat. No. 5,623,005 discloses naphtho[2,1-b]pyrans substituted at the 6 position of the naphthyl portion of the naphthopyran compound with an amino group.

The present invention relates to novel 6-aryl substituted 3H-naphtho[2,1-b]pyran compounds having certain substituents at the 3-position of the pyran ring. Other substituents may also be present optionally at the number 7, 8, 9 or 10 carbon atoms. The naphthopyrans of the present invention have unexpectedly been found to demonstrate a hypsochromic wavelength shift in the visible spectrum at which the maximum absorption of the activated (colored) form of the photochromic compound, i.e., the lambda max (Vis), occurs, thereby resulting in activated colors ranging from yellow to orange. Photochromic compounds of the present invention include compounds that exhibit acceptable photochromic performance properties, i.e., activated intensity, coloration rate and fade rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel 6-aryl substituted 3H-naphtho [2,1-b]pyrans having activated colors ranging from yellow to orange may be prepared. These compounds may be described as 6-aryl substituted 3H-naphtho[2,1-b]pyrans having certain substituents at the 3 position of the pyran ring. Certain substituents may also be present at the number 7, 8, 9 or 10 carbon atoms of the naphtho portion of the compounds. These compounds may be represented by the following graphic formula I in which the numbers 1 through 10 within the depicted ring-system represent the numbers of the ring atoms of the naphthopyran:

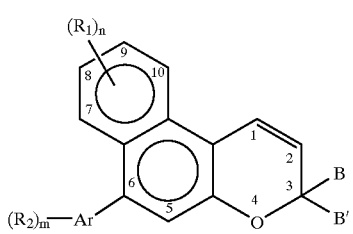

In graphic formula I, each $R_1$ and each $R_2$ may be $C_1$–$C_6$ alkyl, $C_1$–$C_6$ alkoxy, chloro or fluoro; and m and n are each the integers 0, 1, or 2. When m and n are 2, each $R_1$ and $R_2$ may be the same or different. More preferably, each $R_1$ and each $R_2$ are $C_1$–$C_3$ alkyl, $C_1$–$C_3$ alkoxy, or fluoro. Most preferably, $R_1$ and $R_2$ are each $C_1$–$C_3$ alkyl or $C_1$–$C_3$ alkoxy.

Ar in graphic formula I may be phenyl, naphthyl, thienyl, benzothienyl, furanyl, benzofuranyl or pyridyl. Preferably Ar is phenyl or naphthyl.

B and B' in graphic formula I may each be selected from the group consisting of: (i) the unsubstituted, mono-, di-, and tri-substituted aryl groups, phenyl and naphthyl; (ii) the unsubstituted, mono- and di-substituted heteroaromatic groups pyridyl, furanyl, benzofuran-2-yl, benzofuran-3-yl, thienyl, benzothien-2-yl, benzothien-3-yl, each of said aryl and heteroaromatic substituents in parts (i) and (ii) being selected from the group consisting of di($C_1$–$C_6$)alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, acryloxy, methacryloxy, chloro and fluoro; (iii) the groups represented by the following graphic formulae:

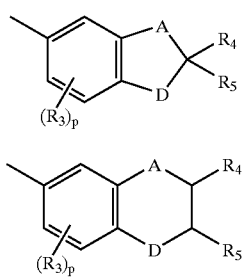

wherein A may be carbon or oxygen and D may be oxygen or substituted nitrogen, provided that when D is substituted nitrogen, A is carbon, said nitrogen substituents being selected from the group consisting of hydrogen, $C_1$–$C_6$ alkyl, and $C_2$–$C_6$ acyl; each $R_3$ is $C_1$–$C_6$ alkyl, $C_1$–$C_6$ alkoxy, hydroxy, chloro or fluoro; $R_4$ and $R_5$ are each hydrogen or $C_1$–$C_6$ alkyl; and p is the integer 0, 1, or 2; (iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)cycloalkyl, chloro($C_3$–$C_6$)cycloalkyl, and fluoro($C_3$–$C_6$)cycloalkyl; and (v) the group represented by the following graphic formula:

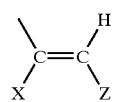

wherein X in graphic formula IIC may be hydrogen or $C_1$–$C_4$ alkyl and Z in graphic formula IIC may be selected from the unsubstituted, mono-, and di-substituted members of the group consisting of naphthyl, phenyl, furanyl, and thienyl, each of said group substituents in this part (v) being $C_1$–$C_4$ alkyl, $C_1$–$C_4$ alkoxy, fluoro, or chloro; or (vi) B and B' taken together form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, cyclododecylidene; saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1]nonan-9-ylidene, bicyclo[4.3.2]undecane, and saturated $C_7$–$C_{12}$ spiro-tricyclic hydrocarbon rings, e.g., tricyclo[$2.2.1.0^{2,6}$] heptylidene, tricyclo[$3.3.1.1^{3,7}$]decylidene, i.e., adamantylidene, and tricyclo[$5.3.1.1^{2,6}$]dodecylidene, each of said fluoren-9-ylidene substituents being selected from the group consisting of $C_1$–$C_4$ alkyl, $C_1$–$C_4$ alkoxy, fluoro and chloro.

More preferably, B and B' are each selected from the group consisting of: (i) phenyl, mono-substituted phenyl, and di-substituted phenyl; (ii) the unsubstituted, mono- and di-substituted heteroaromatic groups furanyl, benzofuran-2-yl, thienyl, and benzothien-2-yl, each of said phenyl and heteroaromatic substituents being selected from the group consisting of di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro; (iii) the groups represented by the graphic formulae IIA and IIB, wherein A is carbon and D is oxygen, $R_3$ is $C_1$–$C_3$ alkyl or $C_1$–$C_3$ alkoxy, $R_4$ and $R_5$ are each hydrogen or $C_1$–$C_4$ alkyl, and p is the integer 0 or 1; (iv) $C_1$–$C_4$ alkyl; and (v) the group represented by the graphic formula IIC wherein X is hydrogen or methyl and Z is phenyl or mono-substituted phenyl, said phenyl substituent being selected from the group consisting of $C_1$–$C_3$ alkyl, $C_1$–$C_3$ alkoxy, and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

Most preferably, B and B' are each selected from the group consisting of (i) phenyl, mono- and di-substituted phenyl, (ii) the unsubstituted, mono- and di-substituted heteroaromatic groups furanyl, benzofuran-2-yl, thienyl, and benzothien-2-yl, each of said phenyl and heteroaromatic substituents being selected from the group consisting of $C_1$–$C_3$ alkyl, $C_1$–$C_3$ alkoxy and fluoro; and (iii) the group represented by graphic formula IIA, wherein A is carbon and D is oxygen, $R_3$ is $C_1$–$C_3$ alkyl or $C_1$–$C_3$ alkoxy, $R_4$ and $R_5$ are each hydrogen or $C_1$–$C_3$ alkyl, and p is the integer 0 or 1; or (iv) B and B' taken together form fluoren-9-ylidene, adamantylidene, bornylidene, norbornylidene, or bicyclo[3.3.1]nonan-9-ylidene.

Compounds represented by graphic formula I may be prepared by the following Reactions A through E. Compounds represented by graphic formula V or VA are either purchased or prepared by Friedel-Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent possible phenyl substituents.

Reaction A

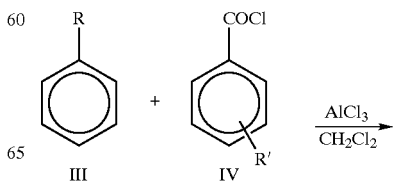

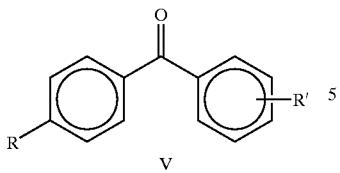

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound. Propargyl alcohols having a B or B' group represented by graphic formula IIC may be prepared by the methods described in U.S. Pat. No. 5,274,132, column 2, lines 40 to 68, which disclossure is incorporated herein by reference.

Reaction B

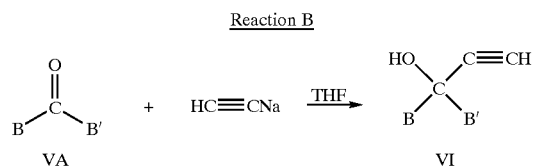

In Reaction C, the compounds represented by graphic formula VII, some of which are commercially available, are condensed with methanol in the presence of a catalytic amount of an acid such as sulfuric acid to form the corresponding methyl arylacetate represented by graphic formula VIII.

Reaction C

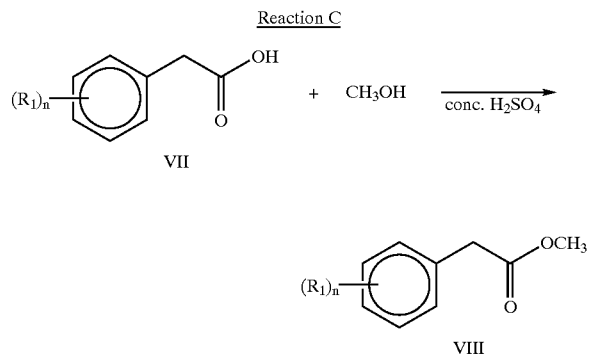

In Reaction D, compound VIII is reacted with the substituted aryl methyl ketone represented by graphic formula IX in the presence of sodium hydride, resulting in a mixture of the tautomers represented by graphic formulae XA and XB. This reaction is further described in C. R. Hauser et al., *Organic Reactions*, Vol 8, page 126 (1954). The tautomers are cyclized by heating, e.g., at about 70° C., in the presence of acid such as phosphoric acid, to the naphthol represented by graphic formula XI. Cyclization of pyridyl substituted compounds is described generally in C. R. Hauser et al, A New Method for the Synthesis of Certain Benz[a]acridines, *J. Amer. Chem. Soc.*, Vol. 77, pages 3858–3860 (1955).

Reaction D

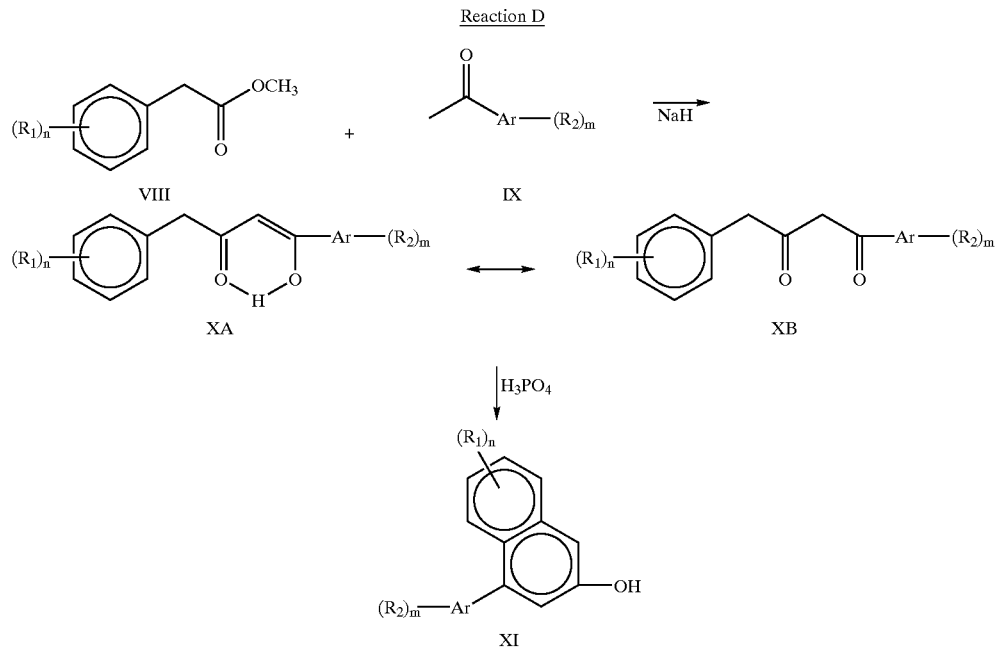

In Reaction E, the compound represented by graphic formula XI is coupled with a propargyl alcohol represented by graphic formula VI in the presence of a catalytic amount of an acid, e.g., p-toluene sulfonic acid in a suitable solvent such as chloroform to produce compounds represented by graphic formula I.

Reaction E

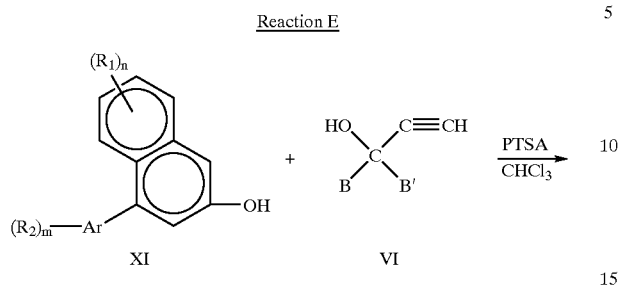

Compounds represented by graphic formula I wherein n is 0 and the —Ar—$(R_2)_m$ group is phenyl, alkyl substituted phenyl or halo substituted phenyl may be prepared by the following Reactions F and G.

In Reaction F, 2-naphthol (graphic formula XII) is reacted with the substituted or unsubstituted benzene represented by graphic formula XIII, wherein $R_2'$ is hydrogen, $C_1$–$C_6$ alkyl, chloro or fluoro, in the presence of aluminum chloride to form the 4-aryl-2-tetralone represented by graphic formula XIV. Compound XIV is aromatized via either a sequence of bromination and dehydrohalogenation or under strong basic conditions in air to form the 4-aryl-2-naphthols represented by graphic formula XV. This procedure is described in V. A. Koptyug et al., *Zh. Org. Khim.*, Vol. 7, pages 2398–2403 (1971).

Reaction F

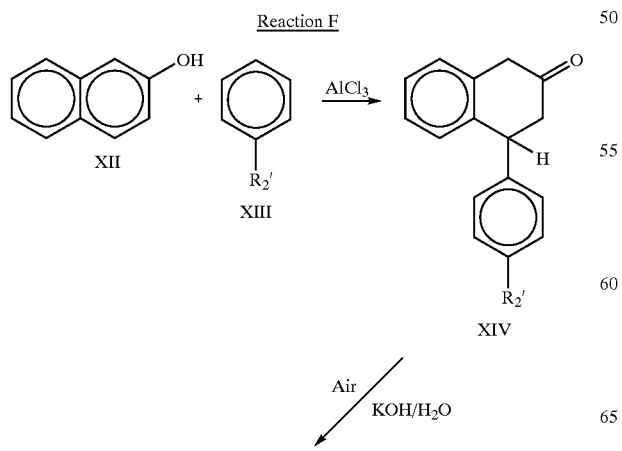

-continued

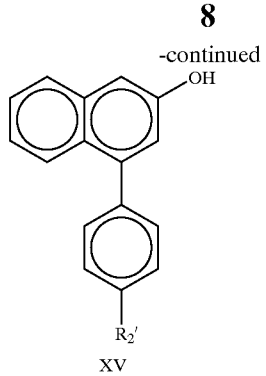

In Reaction G, the compound represented by graphic formula XV is coupled with the propargyl alcohol represented by graphic formula VI in the presence of a catalytic amount of an acid, e.g., dodecylbenzene sulfonic acid (DBSA) as in Reaction E to produce compounds represented by graphic formula Ia.

Reaction G

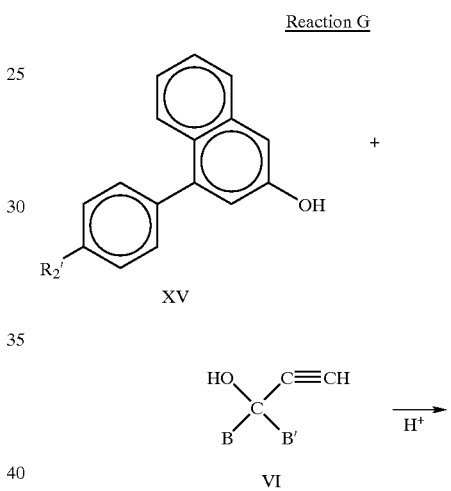

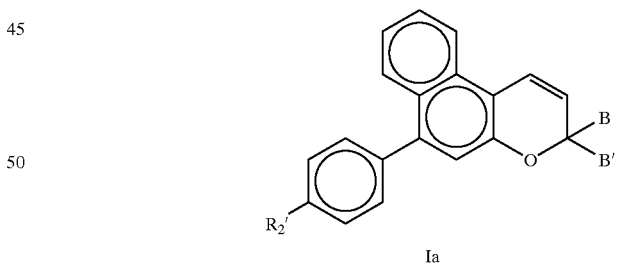

Compounds represented by graphic formula I may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. The 6-aryl or heteroaromatic substituted naphtho[2,1-b]pyrans represented by graphic formula I exhibit color changes from colorless to colors ranging from yellow to orange.

Examples of contemplated naphthopyran compounds within the scope of the invention include the following:

(a) 6-(4-methoxyphenyl)-8,9-dimethoxy-3,3-diphenyl-3H-naphtho [2,1-b]pyran;

(b) 6-(4-methoxyphenyl)-8,9-dimethoxy-3-(2-fluorophenyl)-3-(4-methoxyphenyl)-3H-naphtho[2,1-b]pyran;

(c) 6-phenyl-8,9-dimethoxy-3,3-diphenyl-3H-naphtho[2,1-b]pyran;

(d) 6-phenyl-8,9-dimethoxy-3-(2-fluorophenyl)-3-(4-methoxyphenyl)-3H-naphtho[2,1-b]pyran.

(e) 6-(4-methylphenyl)-3-(2-fluorophenyl)-3-(4-methoxyphenyl)-3H-naphtho[2,1-b]pyran; and (f) 6-(4-methylphenyl)-3,3-diphenyl-3H-naphtho[2,1-b]pyran.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers (or substances containing same) and which color when activated to an appropriate hue. The photochromic compounds of the present invention may be associated with, e.g., incorporated in, i.e., dissolved or dispersed in, a polymeric organic host material used to prepare photochromic articles.

Other than where otherwise indicated, all numbers expressing wavelengths, quantities of ingredients or reaction conditions used herein are to be understood as modified in all instances by the term "about".

Examples of complementary organic photochromic compounds include other naphthopyrans, chromenes and oxazines, substituted 2H-phenanthro[4,3-b]pyran and 3H-phenanthro[1,2-b]pyran compounds, benzopyran compounds having substituents at the 2-position of the pyran ring including a dibenzo-fused 5 member heterocyclic compound and a substituted or unsubstituted heterocyclic ring, such as a benzothieno or benzofurano ring fused to the benzene portion of the benzopyrans, spiro(benzindoline) naphthopyrans, spiro(indoline)benzopyrans, spiro(indoline) naphthopyrans, spiro(indoline)quinopyrans, spiro(indoline) pyrans, spiro(indoline)napthoxazines, spiro(indoline) pyridobenzoxazines, spiro,(benzindoline) pyridobenzoxazines, spiro(benzindoline)naphthoxazines, spiro(indoline)benzoxazines, and mixtures of such photochromic compounds. Many of such photochromic compounds are described in the open literature, e.g., U.S. Pat. Nos. 3,562,172; 3,567,605; 3,578,602; 4,215,010; 4,342, 668; 4,816,584; 4,818,096; 4,826,977; 4,880,667; 4,931, 219; 5,066,818; 5,238,981; 5,274,132; 5,384,077; 5,405, 958; 5,429,774; 5,458,814; 5,466,398; 5,514,817; 5,552, 090; 5,552,091; 5,565,147; 5,573,712; 5,578,252; 5,645,767 and Japanese Patent Publication 62/195383. Spiro(indoline) pyrans are also described in the text, *Techniques in Chemistry*, Volume III, "Photochromism", Chapter 3, Glenn H. Brown, Editor, John Wiley and Sons, Inc., New York, 1971.

Other complementary photochromic substances contemplated are photochromic metal-dithizonates, e.g. mercury dithizonates which are described in, for example, U.S. Pat. No. 3,361,706, fulgides and fulgimides, e.g. the 3-furyl and 3-thienyl fulgides and fulgimides which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, New York (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from 0.05 to 1.0, e.g., from 0.1 to 0.45, milligrams per square centimeter of surface to which the photochromic substance(s) is incorporated or applied.

The photochromic substances of the present invention may be associated with, applied to or incorporated within a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating or film placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

The photochromic compounds of the present invention may be dissolved in an organic solvent or present in an organic polymeric host. The organic solvent may be selected from the group consisting of benzene, toluene, methyl ethyl ketone, acetone, ethanol, tetrahydrofurfuryl alcohol, N-methyl pyrrolidinone, 2-methoxyethyl ether, xylene, cyclohexane, 3-methyl cyclohexanone, ethyl acetate, tetrahydrofuran, methanol, methyl propinate, ethylene glycol and mixtures thereof. Preferably, the organic solvent is selected from the group consisting of acetone, ethanol, tetrahydrofurfuryl alcohol, 2-methoxyethyl ether, 3-methyl cyclohexanone, N-methyl pyrrolidinone and mixtures thereof.

Preferably, the organic polymeric host material is a solid transparent or optically clear material, e.g., materials suitable for optical applications, such as plano and ophthalmic lenses, windows, automotive transparencies, e.g., windshields, aircraft transparencies, plastic sheeting, polymeric films, etc. Examples of polymeric organic host materials are polymers prepared from individual monomers or mixtures of monomers selected from the following groups:

(a) diacrylate or dimethacrylate compounds represented by graphic formula XVI:

XVI

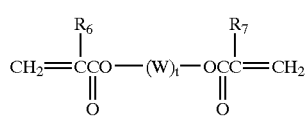

wherein $R_6$ and $R_7$ may be the same or different and are hydrogen or methyl, and W is methylene ($CH_2$), and t is an integer of from 1 to 20;

(b) diacrylate or dimethacrylate compounds represented by graphic formula XVII:

XVII

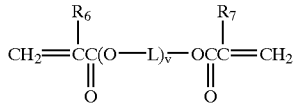

wherein L is $CH_2CH(R_7)$ or $(CH_2)_s$ wherein s is an integer selected from the group consisting of 1, 3 and 4 and v is an integer of from 1 to 50; and (c) an acrylate or a methacrylate compound having an epoxy group represented by graphic formula XVIII:

XVIII

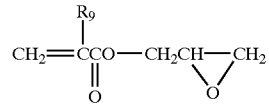

wherein $R_9$ is hydrogen or methyl.

In graphic formulae XVI, XVII and XVIII, like letters used with respect to the definitions of different substituents have the same meaning.

Examples of diacrylate or dimethacrylate compounds, i.e., di(meth)acrylate, represented by graphic formulae XVI include butanediol di(meth)acrylate, hexanediol di(meth)acrylate and nonanediol di(meth)acrylate; examples of compounds represented by graphic formula XVII include diethylene glycol dimethacrylate, triethylene glycol dimethacrylate and poly(oxyalkylene dimethacrylates), e.g., polyethylene glycol (600) dimethacrylate. Examples of acrylate or methacrylate compounds represented by graphic formula XVIII include glycidyl acrylate and glycidyl methacrylate.

Further examples of polymeric organic host materials which may be used with the photochromic compounds described herein include: polymers, i.e., homopolymers and copolymers, of the monomers and mixtures of monomers represented by graphic formulae XVI, XVII and XVIII, bis(allyl carbonate) monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol bismethacrylate monomers, alkoxylated polyhydric alcohol polyacrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly (methyl methacrylate), poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the CR-designation, e.g., CR-307 and CR-407.

The present invention is more particularly described in the following examples which are intended as illustrative only, since numerous modifications and variations therein will be apparent to those skilled in the art.

EXAMPLE 1

Step 1

3,4-Dimethoxyphenylacetic acid (80.0 grams, 0.41 mole), methanol (350 milliliters (mL)) and 2 mL of concentrated sulfuric acid were added to a reaction flask equipped with a Dean-Stark trap condensor and magnetic stirrer. The reaction mixture was maintained at reflux temperature overnight. After removal of unreacted methanol via a rotary evaporator, the product was dissolved in ether. The ether solution was washed twice in a sodium bicarbonate solution, washed twice with water and dried over anhydrous sodium sulfate. The ether was removed on a rotary evaporator, leaving 85 grams of methyl 3,4-dimethoxyphenylacetate as a viscous oil.

Step 2

The acetate from Step 1 (21.0 grams, 0.1 mole) was mixed with sodium hydride (8.0 grams, 0.2 mole of a 60 weight percent dispersion in mineral oil) and dry ether (100 mL) in a reaction flask equipped with a condensor, magnetic stirrer and addition funnel. 4-Methoxyacetophenone (15.0 grams, 0.1 mole) dissolved in dry ether (50 mL) was slowly added over one hour to the mixture. After all the ketone was added, the reaction mixture was maintained at reflux temperature overnight. After cooling to room temperature, the reaction mixture was poured into a mixture of ice and hydrochloric acid resulting in the formation of a white precipitate. By filtering and air drying the precipitate, 26 grams of the desired product was obtained. A nuclear magnetic resonance (NMR) spectrum showed the product to be a tautomeric mixture of keto and enol forms having structures consistent with 1-(4-methoxyphenyl)-4-(3,4-dimethoxyphenyl)-1,3-butadione.

Step 3

The diketone from Step 2 (8.0 grams, 24.3 millimoles) was cyclized by mixing with an 85 percent solution of phosphoric acid (50 mL) in a reaction flask and heating to 70° C. for four hours. The reaction mixture was poured into ice water to produce a reddish, gum-like heavy oil. The oil was extracted with ether, washed with water twice and dried over anhydrous sodium sulfate. After removal of the solvent, ether, on a rotary evaporator, 7.0 grams of a reddish, viscous oil remained. An NMR spectrum showed the product to have a structure consistent with 4-(4-methoxyphenyl)-6,7-dimethoxy-2-naphthol.

Step 4

The naphthol from Step 3 (1.2 grams, 3.8 millimoles) was mixed with 1,1-diphenyl-2-propyn-1-ol (1.04 grams, 5 millimoles), chloroform (25 mL) and toluene (25 mL) in a 250 mL round bottom flask. The reaction was catalyzed by the addition of p-toluene sulfonic acid (0.1 gram) and was kept at 50° C. for four hours. After the reaction mixture cooled to room temperature, the solvents, chloroform and toluene, were removed on a rotary evaporator. The recovered product was dissolved in ether and washed with water twice and dried over anhydrous sodium sulfate. The crude product was purified on a silica gel column, yielding 1.2 grams of a resinous product isolated as an expanded foam. An NMR spectrum showed the product to have a structure consistent with 6-(4-methoxyphenyl)-8,9-dimethoxy-3,3-diphenyl-3H-naphtho[2,1-b]pyran.

EXAMPLE 2

The process of Example 1 was followed except that in Step 4, 7.71 grams (0.03 mole) of 1-(2-fluorophenyl-1-(4-methoxyphenyl)-2-propyn-1-ol (instead of 1,1-diphenyl-2-propyn-1-ol alcohol) was mixed with 7.0 grams (0.023 mole) of the naphthol from Step 3 of Example 1 and chloroform (100 mL) in a 500 mL round bottom flask. The reaction was catalyzed by the addition of p-toluene sulfonic acid (0.1 g), and the mixture was stirred at room temperature for six hours. The reaction mixture was washed with water and dried over sodium sulfate. After evaporation of the solvents at room temperature, silica gel column purification of the reaction mixture yielded 2.4 grams of a foamy, viscous oil. An NMR spectrum showed the product to have a structure consistent with 6-(4-methoxyphenyl)-8,9-dimethoxy-3-(2-fluorophenyl)-3-(4-methoxyphenyl)-3H-naphtho[2,1-b]pyran.

EXAMPLE 3

The process of Example 1 was followed except that in Step 2, acetophenone (11 grams, 0.1 mole) was used instead of 4-methoxyacetophenone. Following silica gel column purification of the crude product, 1.0 gram of desired product crystallized from an ether/hexane mixture. An NMR spectrum showed the product to have a structure consistent with 6-phenyl-8,9-dimethoxy-3,3-diphenyl-3H-naphtho[2,1-b] pyran.

EXAMPLE 4

The process of Example 1 was followed except that in Step 2, acetophenone (11 grams, 0.1 mole) was used instead of 4-methoxyacetophenone and in Step 4, 1-(4-methoxyphenyl)-1-(2-fluorophenyl)-2-propyn-1-ol (1.3 grams, 5 millimoles) was used instead of 1,1-diphenyl-2-propyn-1-ol and toluene (50 mL) was used instead of a mixture of toluene and chloroform. The reaction was catalyzed by the addition of dodecylbenzene sulfonic acid. Silica gel column purification of the crude product yielded 1.0 gram of a resinous product isolated as an expanded foam. An NMR spectrum showed the product to have a structure consistent with 6-phenyl-8,9-dimethoxy-3-(2-fluorophenyl)-3-(4-methoxyphenyl)-3H-naphtho[2,1-b]pyran.

EXAMPLE 5

Step 1

2-Naphthol (36 grams, 0.25 mole) and toluene (100 mL) were added to a reaction flask. The mixture was stirred at room temperature while aluminum chloride (100 grams, 0.75 mole) was added slowly over one hour. The reaction mixture was maintained between 20° C. and 25° C., protected from moisture and stirred for an additional 20 hours. The resulting deep red solution was carefully poured into a 3000 mL beaker containing ice. The organic phase was separated, washed with water, washed with a 2 percent solution of sodium hydroxide and rewashed with water. The toluene was removed on a rotary evaporator leaving 52 grams of a tan oil. An NMR spectrum showed the product to have a structure consistent with 4-(4-methylphenyl)-2-tetralone.

Step 2

The 4-(4-methylphenyl)-2-tetralone from Step 1 (20 grams), ethylene glycol (20 grams) and potassium hydroxide (40 grams) were added to a stainless steel beaker. The mixture was heated and maintained at 150° C. for 30 minutes. After cooling, the contents of the beaker were added to a flask containing water and methylene chloride (50 mL). After stirring, the methylene chloride was discarded and the aqueous layer was acidified. The aqueous mixture was extracted with methylene chloride, and the organic phase was separated. The solvent was removed on a rotary evaporator leaving 5 grams of a dark oil. An NMR spectrum showed the product to have a structure consistent with 4-(4-methylphenyl)-2-naphthol.

Step 3

About half of the 4-(4-methylphenyl)-2-naphthol from Step 2, 1,1-diphenyl-2-propyn-1-ol (3 grams) and toluene (50 mL) were added to a reaction flask. The mixture was stirred at 50° C., two drops of dodecylbenzene sulfonic acid were added, and the mixture was maintained at 50° C. for two hours. The mixture was cooled and the solvent was removed on a rotary evaporator. The residue was purified on a silica gel column using 2:1 hexane:ethyl acetate as the elutant. The desired fractions were combined and the solvents were removed on a rotary evaporator leaving 1.5 grams of a resinous product recovered as an expanded foam. An NMR spectrum showed the product to have a structure consistent with 6-(4-methylphenyl)-3,3-diphenyl-3H-naphtho[2,1-b]pyran.

EXAMPLE 6

The process of Example 5 was followed except that in Step 3, 1-(4-methoxyphenyl)-1-(2-fluorophenyl)-2-propyn-1-ol (3 grams) was used instead of 1,1-diphenyl-2-propyn-1-ol. The mixture was stirred at 50° C., 2 drops of dodecylbenzene sulfonic acid were added, and the mixture was maintained at 50° C. for two hours. The mixture was cooled and the solvent was removed on a rotary evaporator. The residue was purified on a silica gel column using 2:1 hexane:ethyl acetate as the elutant. The desired fractions were combined and the solvents were removed on a rotary evaporator leaving 1.4 grams of a resinous product recovered as an expanded foam. An NMR spectrum showed the product to have a structure consistent with 6-(4-methylphenyl)-3-(2-fluorophenyl)-3-(4-methoxyphenyl)-3H-naphtho[2,1-b]pyran.

COMPARATIVE EXAMPLE A

Step 1

6-Bromo-2-naphthol (6.7 grams, 30 millimoles), 1,1-diphenyl-2-propyn-1-ol (7.3 grams, 25 millimoles), p-toluene sulfonic acid (0.2 grams) and toluene (100 mL) were added to a 500 mL reaction flask. The mixture was stirred at room temperature overnight. After two water washes and drying over anhydrous sodium sulfate, the toluene was removed under a vacuum. The residue was crystallized from ether to yield 11.1 grams of yellow crystals, 8-bromo-3,3-diphenyl-3H-naphtho[2,1-b]pyran, having a melting point of 148–149° C.

Step 2

The 8-bromo-3,3-diphenyl-3H-naphtho[2,1-b]pyran (6.2 grams, 15 millimoles) of Step 1, phenylboric acid (3.7 grams, millimoles), tetrakis (triphenylphosphine)palladium (0.6 gram), sodium carbonate (6.4 grams, 60 millimoles) and toluene (100 mL) were added to a 500 mL reaction flask equipped with a magnetic stirrer. The reaction mixture was degassed under vacuum, then refilled with nitrogen. This process was repeated several times. The reaction mixture was then heated to reflux under nitrogen overnight. After filtering through a silica gel column and removing the solvents, the product was washed with ether to yield 5.7 grams of a white solid having a melting point of 191–192° C. An NMR spectrum showed the product to have a structure consistent with 8-phenyl-3,3-diphenyl-3H-naphtho[2,1-b] pyran.

EXAMPLE 7

Part A

Testing was done with the photochromic compounds described in Examples 1–6 and the Comparative Example in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for at least 2 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 75° F. (23.9° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. A collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density (ΔOD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: ΔOD=log(100/% Ta), where % Ta is the percent transmittance in the activated state and the logarithm is to the base 10.

The optical properties of the photochromic compound in the test squares are reported in Table 1. The Δ OD/Min, which represents the sensitivity of the photochromic compound's response to UV light, was measured over the first five (5) seconds of UV exposure, then expressed on a per minute basis. The saturation optical density (Δ OD@ Sat) was taken under identical conditions as the Δ OD/Min, except UV exposure was continued for 20 minutes. The lambda max (Vis) is the wavelength in the visible spectrum at which the maximum absorption of the activated (colored) form of the photochromic compound in a test square occurs. The lambda max (Vis) wavelength was determined by testing the photochromic test square polymerizates of Part A in a Varian Cary 3 UV-Visible spectrophotometer. The lambda (λ) max (UV) is the wavelength in the ultraviolet range closest to the visible spectrum at which the absorption of the photochromic compound occurs. This absorption was also determined with the same spectrophotometer. The bleach rate (T ½) is the time interval in seconds for the absorbance of the activated form of the photochromic compound in the test squares to reach one half the highest absorbance at room temperature (75° F., 23.9° C.) after removal of the source of activating light. Results for the photochromic compounds tested are listed in Table 1.

TABLE 1

| Example Compounds | (λ) max (VIS) | (λ) max (UV) | ΔOD/MIN sensitivity | ΔOD @ saturation | Bleach T 1/2 |
|---|---|---|---|---|---|
| 1 | 424 | 369 | 0.18 | 0.16 | 34 |
| 2 | 455 | 368 | 0.27 | 0.55 | 149 |
| 3 | 433 | 367 | 0.21 | 0.13 | 22 |
| 4 | 455 | 367 | 0.24 | 0.46 | 123 |
| 5 | 434 | 358 | 0.23 | 0.10 | 26 |
| 6 | 463 | 358 | 0.24 | 0.33 | 89 |
| Comparative Example A | 466 | 355 | 0.20 | 0.09 | 22 |
| Comparative Example B* | 436 | 346 | 0.14 | 0.07 | 24 |

*3,3-diphenyl-3H-naphtho[2,1-b]pyran (U.S. Pat. No. 3,567,605)

The compounds of Examples 1–6 demonstrate a bathochromic shift for lambda max (UV) as compared to the compound of the Comparative Example B. Comparing the lambda max optical properties of the compound of Example 5 with Comparative Examples A and B, all of which compounds have identical B and B' groups, demonstrates that an aryl substituent at the 6 position (Example 5) has a minimal effect on the lambda max (vis), vis-a-vis, (Comparative Example B), whereas an aryl substituent at the 8 position causes a large bathochromic shift.

The present invention has been described with reference to specific details of particular embodiments thereof. It is not intended that such details be regarded as limitations upon the scope of the invention except insofar as to the extent that they are included in the accompanying claims.

We claim:

1. A naphthopyran compound represented by the following graphic formula:

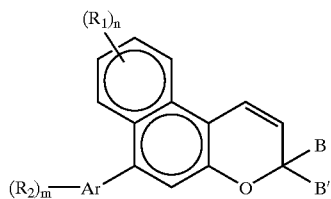

wherein,
(a) each $R_1$ and each $R_2$ are $C_1$–$C_6$ alkyl, $C_1$–$C_6$ alkoxy, chloro, or fluoro, and m and n are each the integers 0, 1 or 2;
(b) Ar is selected from the group consisting of phenyl, naphthyl, thienyl, benzothienyl, furanyl, benzofuranyl and pyridyl; and
(c) B and B' are each selected from the group consisting of:
  (i) the unsubstituted, mono-, di-, and tri-substituted aryl groups, phenyl and naphthyl, said aryl substituents being selected from the group consisting of di($C_1$–$C_6$)alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy ($C_1$–$C_4$)alkyl, acryloxy, methacryloxy, chloro and fluoro; and
  (ii) the groups represented by the following graphic formulae:

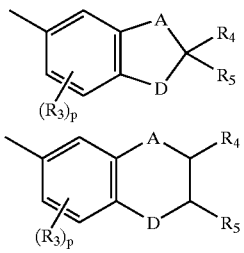

wherein A is carbon or oxygen and D is oxygen or substituted nitrogen, provided that when D is substituted nitrogen, A is carbon, said nitrogen substituents being selected from the group consisting of hydrogen, $C_1$–$C_6$ alkyl, and $C_2$–$C_6$ acyl; each $R_3$ is $C_1$–$C_6$ alkyl, $C_1$–$C_6$ alkoxy, hydroxy, chloro or fluoro; $R_4$ and $R_5$ are each hydrogen or $C_1$–$C_6$ alkyl; and p is the integer 0, 1, or 2.

2. The naphthopyran of claim 1 wherein,
(a) each $R_1$ and each $R_2$ are $C_1$–$C_3$ alkyl, $C_1$–$C_3$ alkoxy, or fluoro;
(b) Ar is phenyl or naphthyl; and
(c) B and B' are each selected from the group consisting of:
   (i) phenyl, mono-substituted phenyl, and di-substituted phenyl, said phenyl substituents being selected from the group consisting of di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro; and
   (ii) the groups represented by the following graphic formulae:

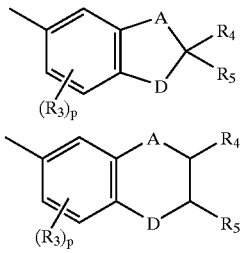

wherein A is carbon and D is oxygen, $R_3$ is $C_1$–$C_3$ alkyl or $C_1$–$C_3$ alkoxy, $R_4$ and $R_5$ are each hydrogen or $C_1$–$C_4$ alkyl; and p is the integer 0 or 1.

3. The naphthopyran compound of claim 2 wherein $R_1$ and $R_2$ are each $C_1$–$C_3$ alkyl or $C_1$–$C_3$ alkoxy, and m and n are each the integers 0 or 1; and B and B' are each selected from the group consisting of phenyl, mono-, and di-substituted phenyl, each of said phenyl substituents being selected from the group consisting of $C_1$–$C_3$ alkyl, $C_1$–$C_3$ alkoxy and fluoro; and the group represented by the following graphic formula:

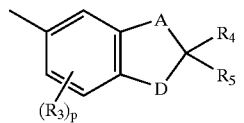

wherein A is carbon and D is oxygen, $R_3$ is $C_1$–$C_3$ alkyl or $C_1$–$C_3$ alkoxy, $R_4$ and $R_5$ are each hydrogen or $C_1$–$C_3$ alkyl, and p is the integer 0 or 1.

4. A naphthopyran compound selected from the group consisting of:
(a) 6-(4-methoxyphenyl)-8,9-dimethoxy-3,3-diphenyl-3H-naphtho[2,1-b]pyran;
(b) 6-(4-methoxyphenyl)-8,9-dimethoxy-3-(2-fluorophenyl)-3-(4-methoxyphenyl)-3H-naphtho[2,1-b]pyran;
(c) 6-phenyl-8,9-dimethoxy-3,3-diphenyl-3H-naphtho[2,1-b]pyran;
(d) 6-phenyl-8,9-dimethoxy-3-(2-fluorophenyl)-3-(4-methoxyphenyl)-3H-naphtho[2,1-b]pyran;
(e) 6-(4-methylphenyl)-3-(2-fluorophenyl)-3-(4-methoxyphenyl)-3H-naphtho[2,1-b]pyran; and
(f) 6-(4-methylphenyl)-3,3-diphenyl-3H-naphtho[2,1-b]pyran.

5. A photochromic article comprising a polymeric organic host material and a photochromic amount of the naphthopyran compound of claim 1.

6. The photochromic article of claim 5 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers, alkoxylated polyhydric alcohol acrylate monomers and diallylidene pentaerythritol monomers.

7. The photochromic article of claim 6 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

8. The photochromic article of claim 7 wherein the photochromic compound is present in an amount of from about 0.05 to 1.0 milligram per square centimeter of organic host material surface to which the photochromic substance(s) is incorporated or applied.

9. The photochromic article of claim 8 wherein the article is a lens.

10. A photochromic article comprising a polymeric organic host material selected from the group consisting of poly(methyl methacrylate), poly(ethylene glycol. bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers and a photochromic amount of the naphthopyran compound of claim 2.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 3.

12. A photochromic article comprising a polymerizate of an optical organic resin monomer and a photochromic amount of the naphthopyran compound of claim 1.

13. The photochromic article of claim 12 wherein the refractive index of the polymerizate is from about 1.48 to about 1.75.

14. The photochromic article of claim 13 wherein the refractive index of the polymerizate is from about 1.495 to about 1.66.

15. A photochromic article comprising, in combination, a solid transparent polymeric organic host material, and a photochromic amount of each of (a) at least one naphthopyran compound of claim 1 and (b) at least one other organic photochromic compound having at least one activated absorption maxima within the range of between about 400 and 700 nanometers.

16. The photochromic article of claim 15 wherein the polymeric organic host material is selected from the group consisting of poly($C_1$–$C_{12}$ alkyl methacrylates), poly (oxyalkylene dimethacrylates), poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly (ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomer and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated bisphenol methacrylate monomers, diisopropenyl benzene monomers and ethoxylated trimethylol propane triacrylate monomers.

18. The photochromic article of claim 15 wherein the organic photochromic compound (b) is selected from the group consisting of naphthopyrans, benzopyrans, phenanthropyrans, spiro(benzindoline)naphthopyrans, spiro (indoline)benzopyrans, spiro(indoline)naphthopyrans, spiro (indoline)quinopyrans, spiro(indoline)pyrans, spiro (indoline)naphthoxazines, spiro(indoline)pyridobenzoxazines, spiro(benzindoline)pyridobenzoxazines, spiro(benzindoline)naphthoxazines, spiro(indoline)-benzoxazines and mixtures of such photochromic compounds.

19. The photochromic article of claim 18 wherein the photochromic compound is present in an amount of from about 0.05 to 1.0 milligram per square centimeter of organic host material surface to which the photochromic substance(s) is incorporated or applied.

20. The photochromic article of claim 19 wherein the article is a lens.

21. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of each of (a) at least one naphthopyran compound of claim 2 and (b) at least one other organic photochromic compound having at least one activated absorption maxima within the range of between about 400 and 700 nanometers.

22. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated bisphenol methacrylate monomers, diisopropenyl benzene monomers and ethoxylated trimethylol propane triacrylate monomers, and a photochromic amount of each of (a) at least one naphthopyran compound of claim 3; and (b) at least one other organic photochromic compound having at least one activated absorption maxima within the range of between about 400 and 700 nanometers.

\* \* \* \* \*